(12) United States Patent
Zamore

(10) Patent No.: US 6,656,550 B1
(45) Date of Patent: Dec. 2, 2003

(54) DILATATION DEVICE OF UNIFORM OUTER DIAMETER

(76) Inventor: Alan M. Zamore, 600 D Rte. 45, Chestnut Ridge, NY (US) 10977

( * ) Notice: Subject to any disclaimer, the term of this patent is extended or adjusted under 35 U.S.C. 154(b) by 0 days.

(21) Appl. No.: 09/558,355

(22) Filed: Apr. 26, 2000

Related U.S. Application Data

(63) Continuation-in-part of application No. 08/947,000, filed on Oct. 8, 1997, now Pat. No. 6,596,818, which is a continuation-in-part of application No. 08/727,145, filed on Oct. 8, 1996, now Pat. No. 5,900,444.

(51) Int. Cl.$^7$ .............................................. B29D 23/00
(52) U.S. Cl. .................... 428/35.7; 428/36.8; 428/36.9; 428/36.92; 604/96.01
(58) Field of Search .......................... 428/35.7, 36.8, 428/36.9, 36.92, 34.1; 604/96.01

(56) References Cited

U.S. PATENT DOCUMENTS

| | | | |
|---|---|---|---|
| 3,616,364 A | 10/1971 | D'Alelio | 204/159.14 |
| 3,642,964 A | 2/1972 | Rausch, Jr. et al. | 264/40 |
| 3,658,670 A | 4/1972 | Holicky et al. | 204/159.15 |
| 3,674,743 A | 7/1972 | Verdol et al. | 260/73 L |
| 3,719,539 A | 3/1973 | Lamb et al. | 156/199 |
| 3,871,908 A | 3/1975 | Spoor et al. | 117/93.31 |
| 3,911,202 A | 10/1975 | Stine et al. | 174/120 SR |
| 4,013,806 A | 3/1977 | Volkert et al. | 427/54 |
| 4,025,407 A | 5/1977 | Chang et al. | 204/159.14 |
| 4,065,589 A | 12/1977 | Lenard et al. | 428/35 |
| 4,101,699 A | 7/1978 | Stine et al. | 428/36 |
| 4,133,731 A | 1/1979 | Hansen et al. | 204/159.17 |
| 4,151,057 A | 4/1979 | St. Clair et al. | 204/159.17 |
| 4,255,552 A | 3/1981 | Schollenberger et al. | 528/50 |
| 4,264,658 A | 4/1981 | Tobias et al. | 428/35 |
| 4,266,005 A | 5/1981 | Nakamura et al. | 430/271 |
| 4,275,180 A | 6/1981 | Clarke | 525/173 |
| 4,289,682 A | 9/1981 | Peters | 260/37 N |
| 4,331,697 A | 5/1982 | Kudo et al. | 427/2 |
| 4,342,793 A | 8/1982 | Skinner et al. | 427/44 |
| 4,358,354 A | 11/1982 | Iida et al. | 204/159.15 |
| 4,443,588 A | 4/1984 | Fukuda et al. | 526/301 |
| 4,444,816 A | 4/1984 | Richards et al. | 428/36 |

(List continued on next page.)

FOREIGN PATENT DOCUMENTS

| | | |
|---|---|---|
| CA | 901410 | 5/1972 |
| EP | 0-214-602 | 3/1987 |
| JP | 61174256 | 8/1986 |
| WO | WO 82/02048 | 6/1982 |
| WO | WO 95/23619 | 9/1995 |
| WO | WO 98/55171 | 12/1998 |
| WO | WO01/19425 A1 | 3/2001 |

OTHER PUBLICATIONS

"Radiation Crosslinked Thermoplastic Polyurethane," published in the journal *International Polymer Science and Technology*, vol. 19, No. 1, pp T/6–T/9 (1992).

*Primary Examiner*—Monique R. Jackson
(74) *Attorney, Agent, or Firm*—Dale L. Carlson; Wiggin & Dana LLP

(57) ABSTRACT

A dilatation device comprising a polymer tube having an essentially uniform outer diameter, with an expandable portion and a less expandable portion, said expandable portion having a wall thickness different than that of said less expandable portion. Said device is formed by providing a tube with an original outer diameter, length and wall thickness; heating the tube; applying pressure to the interior of the tube to expand a portion of said tube to form a balloon having a desired shape and size; releasing the interior pressure and collapsing said balloon; and, simultaneously allowing said portion in which the balloon was formed to radially shrink while longitudinally restraining said portion thereby manipulating the original diameter and length of said tube, said heated and shrunk portion thereby forming an expandable portion in said tube.

15 Claims, 1 Drawing Sheet

U.S. PATENT DOCUMENTS

| | | | | |
|---|---|---|---|---|
| 4,490,421 A | 12/1984 | Levy | ................... | 428/35 |
| 4,552,815 A | 11/1985 | Dreher et al. | ................... | 428/415 |
| 4,567,083 A | 1/1986 | Arioka et al. | ................... | 428/141 |
| 4,607,084 A | 8/1986 | Morris | ................... | 525/454 |
| 4,608,984 A | 9/1986 | Fogarty | ................... | 128/344 |
| 4,654,233 A | 3/1987 | Grant et al. | ................... | 427/379 |
| 4,687,689 A | 8/1987 | Yazaki et al. | ................... | 428/35 |
| 4,762,884 A | 8/1988 | Goyert et al. | ................... | 525/28 |
| 4,820,782 A | 4/1989 | Ueno | ................... | 525/454 |
| 4,871,811 A | 10/1989 | Gaku et al. | ................... | 525/148 |
| 4,897,433 A | 1/1990 | Sugo et al. | ................... | 522/116 |
| 4,948,859 A | 8/1990 | Echols et al. | ................... | 528/28 |
| 5,084,529 A | 1/1992 | Crano | ................... | 525/455 |
| 5,109,097 A | 4/1992 | Klun et al. | ................... | 528/75 |
| 5,116,652 A | 5/1992 | Alzner | ................... | 428/36.9 |
| 5,236,978 A | 8/1993 | Selvig et al. | ................... | 524/81 |
| 5,266,669 A | 11/1993 | Onwunaka et al. | ................... | 528/28 |
| 5,284,883 A | 2/1994 | Ueno et al. | ................... | 522/79 |
| 5,328,940 A | 7/1994 | Zimmer | ................... | 522/31 |
| 5,334,201 A | 8/1994 | Cowan | ................... | 623/1 |
| 5,336,585 A | 8/1994 | Takahashi et al. | ................... | 430/284 |
| 5,374,704 A | 12/1994 | Müller et al. | ................... | 528/66 |
| 5,382,633 A | 1/1995 | Scott et al. | ................... | 525/279 |
| 5,438,106 A | 8/1995 | Siranovich et al. | ................... | 525/440 |
| 5,455,308 A | 10/1995 | Bastiaansen | ................... | 525/407 |
| 5,511,965 A | 4/1996 | Batdorf et al. | ................... | 425/381 |
| 5,576,072 A | 11/1996 | Hostettler et al. | ................... | 427/532 |
| 5,733,496 A | 3/1998 | Avellanet | ................... | 264/470 |
| 5,755,707 A * | 5/1998 | Miyagawa et al. | ................... | 604/96 |
| 5,786,426 A * | 7/1998 | Sperling et al. | ................... | 525/131 |
| 5,849,846 A * | 12/1998 | Chen et al. | ................... | 525/166 |
| 5,900,444 A | 5/1999 | Zamore | ................... | 522/137 |
| 5,993,415 A | 11/1999 | O'Neil et al. | ................... | 604/96 |
| 5,998,551 A | 12/1999 | O'Neil et al. | ................... | 525/426 |
| 6,022,341 A * | 2/2000 | Lentz | ................... | 604/523 |
| 6,090,099 A * | 7/2000 | Samson et al. | ................... | 604/527 |
| 6,238,408 B1 * | 5/2001 | Kawabata et al. | ................... | 606/192 |

\* cited by examiner

DILATATION DEVICE OF UNIFORM OUTER DIAMETER

CROSS REFERENCE TO RELATED APPLICATIONS

This patent application claims priority of U.S. patent application Ser. No. 08/947,000 entitled "Irradiation Conversion of Thermoplastic to Thermoset Polymers" that was filed on Oct. 8, 1997 now U.S. Pat. No. 6,596,818, which is a continuation-in-part of commonly owned U.S. patent application Ser. No. 08/727,145 filed on Oct. 8, 1996, now U.S. Pat. No. 5,900,444. U.S. patent application Ser. No. 08/947,000 and U.S. Pat. No. 5,900,444 are incorporated herein by reference in their entirety.

FIELD OF INVENTION

This invention relates generally to dilatation devices and, more specifically, to balloon catheters having an essentially uniform outer diameter with a variable wall thickness of desire compliance and break pressure upon inflation.

BACKGROUND OF THE INVENTION

In coronary balloon catheters, a continuous length of polymer tube is utilized to form a balloon. Typically, the balloon portion of the tube must be wrapped or folded to take up the slack of the balloon portion and to insure that the outer diameter of the wrapped or folded tube is sufficiently small to be insertable into blood vessels.

Factors to be considered when fabricating dilatation devices include: (a) minimizing the outer diameter ("OD") of the tube and/or the balloon portion to enable it to be passed easily through the desired vessels or organs of the body, (b) providing sufficient strength to the tube without undesired kinking, bending or twisting to enable it to be passed easily to the site of the occlusion being treated, and (c) insuring that the balloon, once inflated at the site of the occlusion, has a desired compliance and tensile strength to allow expansion in a controlled manner to a desired inflated diameter of the balloon, and to minimize the chance of bursting the balloon.

In the past, designs intended to accommodate some of these factors have included: (a) a double-layered balloon comprising an inner non-elastic balloon and an outer elastic balloon, as disclosed in U.S. Pat. No. 4,608,984; (b) an expandable and collapsible balloon reinforced by knitted fabric to insure that the balloon cannot expand beyond a predetermined diameter; (c) the use of high molecular weight polymer, such as polyethylene terephthalate ("PET") polyester, to provide a bi-axially oriented, flexible polymeric balloon having a burst pressure of at least 200 psi and a radial expansion beyond the desired inflated diameter of less than 5% at 200 psi, as disclosed in U.S. Pat. No. 4,490,421; and (d) the use of fiberglass or shell wire fused over a polyurethane catheter to reinforce the tube at the beginning and ending of the thinned (balloon) portion. In addition, U.S. Pat. No. 5,348,538 discloses a method to make a (rigid polyurethane or PET) balloon catheter having a non-linear compliance curve formed by shrinking the balloon tube to a diameter below its original diameter. The resulting balloon catheter is said to be compliant if it exhibits a non-compliant compliance curve when expanded beyond its original diameter. U.S. Pat. No. 5,733,496 also discloses a method of stiffening a compliant polymer tube, upon manufacture thereof, by exposing the tube to e-beam radiation.

An important problem associated with conventional catheter balloon systems is that the balloon "bag," even when wrapped or folded in order to minimize its diameter, possesses a larger outer diameter than that associated with the remainder of the catheter tube. Although tubing of non-uniform outer diameter is known in the tube extrusion field, as illustrated by the disclosures of U.S. Pat. No. 5,511,965, such non-uniform tube requires complicated mandrels and mechanical dies, making this application impractical in the balloon catheter field. Indeed, the larger diameter balloon portion poses a risk of difficulty in threading the tube into the occluded blood vessel during use. Therefore, there is a need for an easily constructed catheter balloon capable of unitary and integral construction having a uniform or near uniform outer diameter in order to provide relative ease of insertion into a blood vessel or body cavity.

Other uses for tubes with an expandable portion (balloon portion) of uniform OD relative to a less expandable portion (non-balloon portion) include gastroenterology catheters, urethral catheters, neurological catheters, endotrachial catheters, or peritonieal drains. In addition, such a tube has other potential applications of a medical or non-medical nature, wherein it might be desirable to thread a tube into a restricted size opening and then inflate the tube radially to that opening so as to either block the opening, reduce an obstruction or prevent the tube from being inadvertently withdrawn.

The term "unitary construction" or "continuous" as used herein, when applied to an article of manufacture such as a balloon catheter tube, means an article of manufacture which is fabricated in a single piece, as opposed to an article of manufacture which is fabricated by the joining together of separate pieces. Thus, an article of unitary construction is seamless. Similarly, the term "integral" as used herein, when applied to adjacent portions of an article, means that there is no joint, seam, or material boundary between the subject portions.

Further, the term "polymer tube" refers to one which has memory either inherent or induced by some mechanical process such as stretching or preferably by crosslinking the material by radiation or heat.

SUMMARY OF THE INVENTION

Dilatation devices have a variety of uses in the medical field and in industrial and commercial applications where narrow areas must be dilated. The present invention discloses a device made from a continuous length of tube that overcomes the limitations of the prior art. Further, a method of forming these devices is disclosed.

In one aspect, the present invention relates to a dilatation device comprising a continuous length of polymer tube having an essentially uniform outer diameter with an integral expandable portion and a less expandable portion, said expandable portion having a wall-thickness less than that of said less expandable portion.

Preferably, the polymer tube is comprised of a polymer imparted with memory. Memory may be imparted in a variety of ways, including crosslinking by irradiating or heating the material. Ideal crosslinked polymers include crosslinked thermoplastic elastomers, crosslinked thermoplastic polymers, crosslinked polyamide polymers, crosslinked polyamide elastomer block co-polymers, crosslinked polyester elastomer block co-polymers, crosslinked thermoplastic polyurethane polymers, crosslinked polyethylene polymers, or crosslinked polyethylene co-polymers. Examples of suitable thermoplastic elastomers include a block co-polymer, a graft co-polymer, a blend of elastomers and thermoplastics, or an ionomer.

Further, polyethylene terephthalate homopolyester polymers or polybutylene terephthalate homopolyester polymers may be suitable tube materials.

The crosslinking of the material may be performed by heat crosslinking in the presence of a heat-activated catalyst, such as an organic peroxide. Further, the crosslinking may be performed by photonic radiation, such as high energy electron beam particles, gamma radiation particles, UV radiation and combinations thereof. In addition, such crosslinking may require the presence of monomeric crosslinking agents such as allylic, methacrylic, or acrylic crosslinking monomers which are well known to those skilled in the art. The radiation dosage will depend on the material being used, but will generally range between approximately 0.1 and 250 MegaRads.

The present invention also relates to a preferred process to form the device described above, comprising manipulating a portion of a tube of polymeric material by:

(a) providing a tube with a memory of an original wall thickness, outer diameter and length;

(b) heating said tube;

(c) applying pressure to the interior of the tube to expand a portion of said tube to form a balloon of a desired shape and size, said portion have an original length;

(d) releasing the interior pressure and collapsing said balloon; and, (e) simultaneously allowing said balloon to radially shrink while longitudinally restraining said balloon thereby manipulating the wall thickness of said balloon as it shrinks, said heated and shrunk balloon thereby forming an expandable portion in said tube.

There are many different ways to form the balloon in the tube which are well known to those skilled in the art. For example, the balloon may be formed in free air or in the presence of a mold. Further, the balloon may be formed by applying pressurized gas or fluids against the interior of the tube.

In one aspect of this process, the balloon is cooled before the interior pressure is released and the balloon is collapsed. The balloon is then reheated in a controlled manner before the expandable portion is radially shrunk.

In a preferred embodiment, the step of longitudinally restraining said portion is performed so as to create a finished tube with an overall length longer than that of the original tube and with a portion containing a thinner wall thickness than the original tube. While the balloon radially shrinks, the portion of the tube in which the balloon was formed is held at a length longer than the original length of said portion. The end result is a longer tube containing a portion with a thinner wall thickness as depicted in FIG. 1. Alternatively, said portion can be longitudinally elongated in a controlled manner during balloon shrinkage so create a tube that is substantially longer than the original tube and with substantially thinner walls.

The process described above results in a tube with an expandable portion and less expandable portion. When the tube is pressurized, the expandable portion inflates to form a balloon while the less expandable portion remains as a tube and does not inflate to form a balloon.

Accordingly, an objective of the present invention is to provide a dilatation device that has a minimal outer diameter ("OD") so as to be passed easily through narrow openings.

Another objective of the present invention is to provide a dilatation device that has sufficient strength but avoids kinking, bending or twisting and is therefore easily passed to the desired location, such as an occlusion being treated.

Yet another objective of the present invention is to provide a dilatation device that has a balloon that when inflated has a desired compliance and tensile strength to allow expansion in a controlled manner to a desired inflated diameter of the balloon.

A further objective of the present invention is to provide an easily constructed catheter balloon capable of unitary and integral construction having a uniform or near uniform outer diameter in order to provide relative ease of insertion into a blood vessel or body cavity.

Yet a further objective of the present invention is to provide a simple method for manufacturing dilatation devices having the characteristics listed above.

These and other aspects will become apparent upon reading the following detailed description of the invention when read in conjunction with the accompanying drawing.

DETAILED DESCRIPTION OF THE INVENTION

Figure 1:
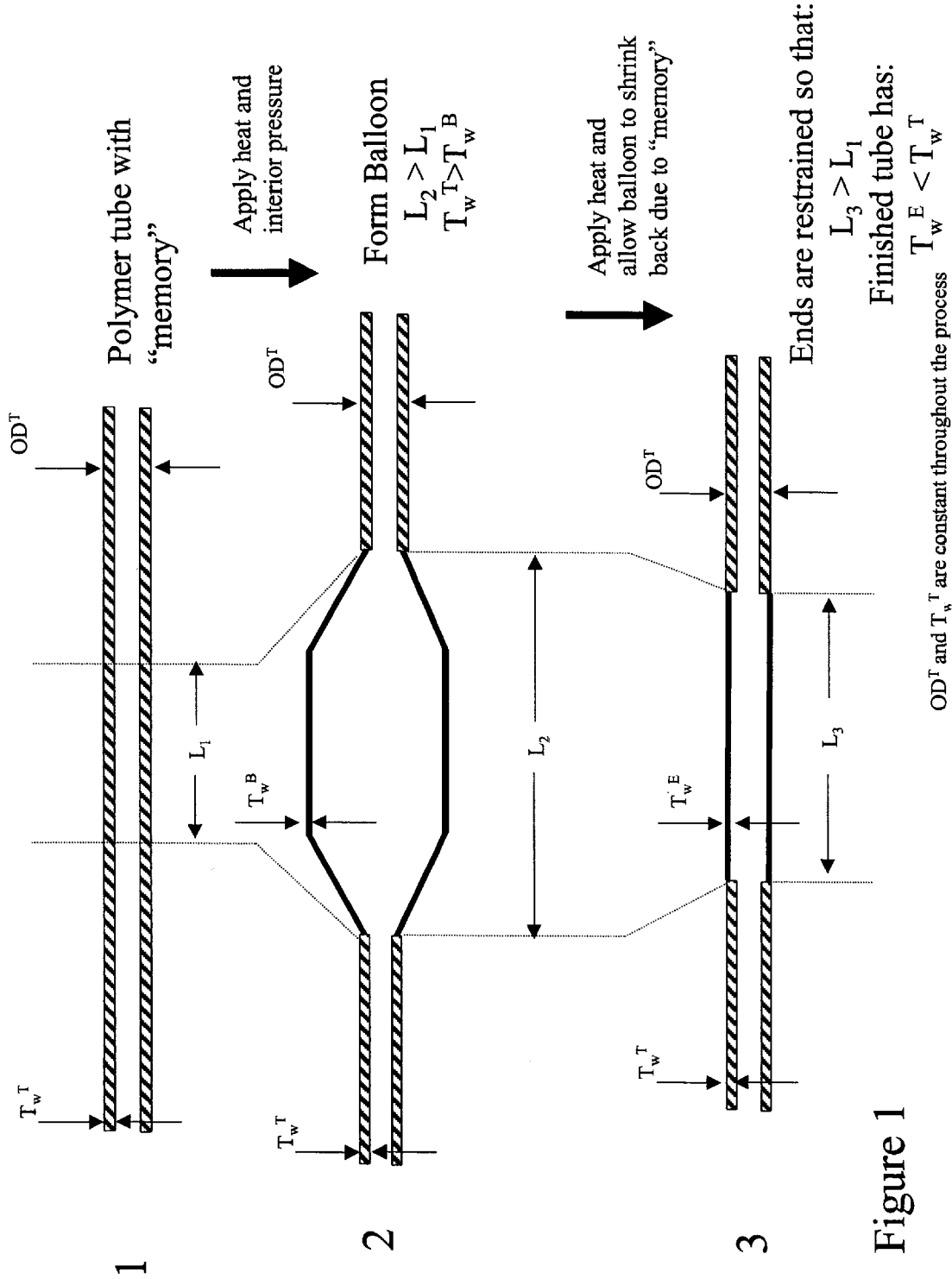
FIG. 1 is a cross-section of a tube of constant outer diameter with reduced wall thickness in selected locations.

Angioplasty balloon catheters are widely used in treating circulatory problems. One issue in their use is the thick overall cross section of the portion of the catheter containing the inflatable balloon. Such an balloon angioplasty catheter is usually made by blow molding a portion of a tube into a thin walled balloon, deflating and then tightly folding the balloon around the catheter. In order to allow compact folding of the balloon, the wall thickness of the balloon must be as thin as possible. However, thinner walled balloons generally have reduced burst pressures. Further, certain strong but stiff materials are difficult to fold tightly even though the balloon formed from the material is thin walled, thereby increasing the catheter's cross section and limiting their usefulness in narrow arterial work. The folded balloon, even when folded tightly, always increases the overall diameter of the tube thereby limiting, to some degree, the size artery into which it can be threaded. The present invention enables the creation of an angioplasty balloon whose diameter is approximately equal to the outer diameter of the catheter from which it was made thereby overcoming the limitations of the prior art. In additional, the present invention creates stronger balloons by allowing thicker walls in the balloon area and/or the catheter tube itself while maintaining the overall diameter of the tube from which it is formed.

This invention takes advantage of the "memory" characteristics that may be imparted to or inherent in a wide variety of materials particularly certain polymers, and more particularly cross-linked polymers. If a shaped polymeric object is crosslinked, heated above its crystalline melting point, reformed into a new shape, and cooled, it will retain that newly formed shape. However, if it is subsequently reheated, the newly formed object will revert to the shape originally maintained after crosslinking but prior to being reformed. This "memory" effect is widely used for shrink tube and shrink wrap film. This invention applies this technology in a novel way, for example, in angioplasty balloon catheter fabrication wherein the availability of a catheter of thinner overall diameter would be of great utility to the medical profession.

In accordance with the present invention and as depicted in FIG. 1, a polymer is first extruded into a continuous tube of a desired length and outside diameter. The type of polymer is chosen based on its ability to retain a "memory." In general, any crosslinkable polymer of sufficient strength for use in angioplasty balloon catheters (or other forms of dilatation devices) is useable in the present invention, as well as PET and other polymers that do not require crosslinking to exhibit memory. Memory is then imparted in the polymer. Depending on the material and process preferences, memory may be imparted by using heat, with or without a catalyst, such as an organic peroxide. Further, memory may be imparted using photonic radiation, such as high energy electron beam particles, gamma radiation particles, UV radiation or combinations thereof, sufficiently to impart memory at a dosage depending on the material used but usually in the range of 0.1 to 250 MegaRads. These methods of imparting memory are described as examples only and are not intended to be limiting. A person skilled in the art would recognize that there are many substantially equivalent methods to impart memory.

FIG. 1 depicts a non-limiting embodiment of the present invention wherein tube 1 is a continuous length of polymer tube with wall thickness $T_W^T$ and outer diameter $OD^T$. A length of the tube ($L_1$) is suitably utilized to form a balloon preferentially by heating a portion of the tube, optionally in the presence of a mold, and applying pressure to the interior of the tube to expand the heated portion. As shown in FIG. 1, tube 2 contains a "balloon" of wall thickness $T_W^B$ and length $L_2$. The outer diameter of the tube $OD^T$ and wall thickness of the tube $T_W^T$ have remained unchanged. Further, in this figure the length of the balloon $L_2$ is shown greater than $L_1$ ($L_2$ can also be equal or less than $L_1$) and the wall thickness of the tube $T_W^T$ is greater than the wall thickness of the balloon $T_W^B$.

The balloon is then collapsed by releasing the interior pressure and removing the mold if used. The tube may be optionally cooled in the mold so that the balloon retains its shape, prior to releasing the pressure to collapse the balloon. If cooled, then the tube should be reheated in a controlled manner. This heating due to "memory" will tend to cause the formed balloon to shrink back to the original dimensions of the tube from which it was formed. However, while this heat is being applied, the ends of the tube are suitably subjected to one of the following restraining alternatives depending on the circumstances related to forming the balloon. The tube may be restrained so as to maintain the same original overall length that the tube exhibited with the formed balloon still in place. Alternatively, the balloon may be longitudinally elongated, preferably to a predetermined length. In either alternative the "memory" effect causes the ballooned portion to return to its original outside diameter but at a longer length than the original tube from which it was formed. After cooling, this ballooned portion forms an expandable portion in the tube and has a reduced wall thickness relative to the remainder of the tube (less expandable portion). This expandable portion thereby contains a susceptibility to preferably expand upon introduction of pressure to the interior of the tube. The finished tube now contains an expandable portion (where the balloon was formed) and a less expandable portion (where no balloon was formed).

As shown in FIG. 1, tube 3 contains an expandable portion in which a balloon can be formed and a less expandable portion that retains its shape as a tube. The expandable portion has a length $L_3$. This portion can be restrained so that $L_3$ is greater than $L_1$ but shorter than $L_2$ (shown). Alternatively, the expandable portion can be longitudinally elongated so that $L_3$ is greater than $L_2$ (not shown). In either case, the wall thickness of the expandable portion $T_W^E$ is less than the wall thickness of the tube (less expandable portion) $T_W^T$, provided that $L_3 > L_1$. The outer diameter of the entire tube (the expandable and less expandable portions) is uniform and is equal to the outer diameter of th original tube (tube 1) $OD^T$.

As stated above, the dilatation device of the present invention is suitably fabricated from a polymer material, preferably thermoplastic. A wide variety of polymers may be used in accordance with the present invention, including thermoplastic polymers and thermoplastic elastomer polymers including block co-polymer thermoplastic elastomers such as polyamide-elastomer block co-polymers which are sold under the trademarks PEBAX, VESTAMID, and GRILAMID by Atochem, Creanova, and American Grilon, respectively, and polyester elastomer block co-polymers such as HYTREL, LOMOD, ECDEL, and ARNITEL, which are manufactured by DuPont, GE, EASTMAN and DSM, respectively. In addition, thermoplastic polyurethanes, such as aliphatic or aromatic polyester, polyether, polycarbonate and other types of polyurethanes may be used. Further, the following polymers may also be used in accordance with the present invention: PET (polyethylene terephthalate); PBT (polybutylene terephthalate); fluoropolymers such as PVDF (polyvinylidene difluoride) such as KYNAR, manufactured by Atochem; fluoroelastomers such as VITON manufactured by Dupont; PVC (polyvinyl chloride); various polyolefins such as polyethylene or the polyethylene co-polymers such as ENGAGE manufactured by Dow, or ethylene propylene co-polymers such as EPDM and EPR; polyamides such as NYLON 12 or 11 manufactured by Atochem and others, NYLON 6 or 6, 6, and other aliphatic or aromatic polyamides; and blends of various polymers. It should be understood that the materials discussed above are merely exemplary of polymers that may be used in accordance with the present invention; and a wide variety of materials can be used, including thermoset materials or castable materials or materials formed from solution, without departing from the spirit of the present invention as long as they possess or can be induced to possess "memory".

The following examples are intended to illustrate, but in no way limit the scope of, the present invention.

EXAMPLES

Example 1

A length of irradiated thin wall polycarbonate TPU tube was heated and a balloon was formed. The balloon was subsequently heated while longitudinally elongating the tube so as to allow the balloon portion to return to its original diameter but at an increased length. After cooling, the tube was re-pressurized and the balloon reappeared in the portion wherein it was originally formed. The finished tube now contains an expandable portion (where the balloon was formed) and a less expandable portion (where no balloon was formed).

Example 2

A length of EBXL TPU tube irradiated at 15 MegaRads of diameter 0.125 in. and wall thickness 0.045 in. was heated and expanded into a balloon. After cooling the balloon wall thickness measured approximately 0.010 in. Subsequently the balloon segment was reheated in a controlled manner. The balloon was allowed to shrink back to its approximate original OD, while being restrained so as to maintain the same overall length of the ballooned portion as the original length of the tube. The tube with the contracted balloon portion was allowed to cool and then pressure was introduced into the tube. The balloon was observed to reappear in the expandable portion where the original balloon was formed. In additional, the wall thickness of this expandable portion was measured to be approximately 0.013 in. after it was allowed to shrink.

Example 3

A length of EBXL TPU tube irradiated at 15 MegaRads of diameter 0.125 in. and wall thickness 0.045 in. was heated and simultaneously longitudinally elongated so as to lengthen the portion to approximately twice its original length. The tube with the expandable portion was allowed to cool and then pressure was introduced into the tube. A balloon was observed to reappear only in the expandable portion. The wall thickness of the lengthened expandable portion measured approximately 0.020 in. However, this method is not preferred because it is difficult to prevent a decrease in the OD of the lengthened expandable portion relative to the OD of the original tube.

Example 4

A preformed angioplasty catheter of crosslinked polyethylene or similar crosslinked material was heated while keeping its overall length constant. The balloon was observed to shrink back to the diameter of the tube. When pressure was applied to the interior of the tube, the balloon reappeared in the same location as originally formed and with a similar shape.

What is claimed is:

1. A dilatation device consisting of a continuous polymer tube having a uniform outer diameter with an integral expandable portion and a less expandable portion, said expandable portion having a wall thickness that is less than that of said less expandable portion.

2. The device of claim 1 wherein the polymer tube is comprised of one or more materials selected from the group consisting of polyethylene terephthalate homopolymester polymers and polybutylene terphthalate homopolyester polymers.

3. A dilatation device consisting of a continuous polymer tube having a uniform outer diameter with an integral expandable portion and a less expandable portion, said expandable portion having a wall thickness that is less than that of said less expandable portion, wherein the tube is comprised of a material containing one or more crosslinked polymers.

4. The device of claim 1 wherein the tube is comprised of a material containing one or more crosslinked thermoplastic elastomers.

5. The device of claim 4 wherein said one or more crosslinked thermoplastic elastomers are selected from the group consisting of a block co-polymer, a graft co-polymer, a blend of elastomers and thermoplastics, and an ionomer.

6. The device of claim 1 wherein the tube is comprised of a material containing one or more crosslinked thermoplastic polyurethane polymers.

7. The device of claim 1 wherein the tube is comprised of a material containing one or more crosslinked polyamide polymers.

8. The device of claim 1 wherein the tube is comprised of a material containing one or more crosslinked polyamide elastomer co-polymers.

9. The device of claim 1 wherein the tube is comprised of a material containing one or more crosslinked polyester elastomer co-polymers.

10. The device of claim 1 wherein the tube is comprised of a material containing one or more crosslinked polyethylene polymers or polyethylene co-polymers.

11. The device of claim 3 wherein said one or more crosslinked polymers are prepared by heat cross-linking in the presence of a heat-activated catalyst.

12. The device of claim 11 wherein said heat activated catalyst is an organic peroxide.

13. The device of claim 3 wherein said crosslinked polymer is crosslinked through the application of photonic radiation.

14. The device of claim 13 wherein said photonic radiation is selected from the group consisting of high energy electron beam particles, gamma radiation particles, UV radiation and combinations thereof.

15. The device of claim 14 wherein said photonic radiation dosage is between approximately 0.1 and 250 MegaRads.

* * * * *